US006866508B2

(12) United States Patent
Anitua Aldecoa

(10) Patent No.: US 6,866,508 B2
(45) Date of Patent: Mar. 15, 2005

(54) DENTAL IMPLANT-CARRIER ASSEMBLY

(76) Inventor: Eduardo Anitua Aldecoa, San Antonio, 15, E-01005-Vitoria (ES)

( * ) Notice: Subject to any disclaimer, the term of this patent is extended or adjusted under 35 U.S.C. 154(b) by 27 days.

(21) Appl. No.: 10/203,464

(22) PCT Filed: Sep. 14, 2001

(86) PCT No.: PCT/ES01/00349

§ 371 (c)(1),
(2), (4) Date: Apr. 7, 2003

(87) PCT Pub. No.: WO02/24102

PCT Pub. Date: Mar. 28, 2002

(65) Prior Publication Data

US 2003/0152890 A1 Aug. 14, 2003

(30) Foreign Application Priority Data

Sep. 19, 2000 (ES) .............................. 20002268

(51) Int. Cl.[7] .................................................. A61C 8/00
(52) U.S. Cl. ....................................................... 433/174
(58) Field of Search ................................. 433/173, 174, 433/172

(56) References Cited

U.S. PATENT DOCUMENTS 5,064,425 A * 11/1991 Branemark et al. ........... 606/72
5,145,371 A * 9/1992 Jorneus ....................... 433/173
5,269,685 A * 12/1993 Jorneus et al. .............. 433/174
5,842,865 A * 12/1998 Bassett et al. ............... 433/174
6,048,204 A * 4/2000 Klardie et al. ............... 433/174
6,053,733 A   4/2000 Aspichueta et al.
6,168,436 B1 * 1/2001 O'Brien ....................... 433/173
6,196,842 B1 * 3/2001 Jorneus ....................... 433/174

FOREIGN PATENT DOCUMENTS

| DE | 43 26 841 A1 | 2/1995 |
| WO | WO 98/03130 A1 | 1/1998 |
| WO | WO 99/17676 A2 | 4/1999 |

* cited by examiner

Primary Examiner—Todd E. Manahan
(74) Attorney, Agent, or Firm—Browdy and Neimark, P.L.L.C.

(57) ABSTRACT

A dental implant-carrier assembly is provided, which is a set of elements formed by a dental implant plus a series of removable carrier elements that allow to simplify the procedure of introducing and installing the dental implant in its final location. The dental implant-carrier assembly includes an improved implant design for hard bones, that comprises new cutting sections and threaded taper designs. The carrier elements include an O-ring seal that improves the connection between elements, as well as new hexagonal protruding elements that act as a reference when installing the implant.

6 Claims, 3 Drawing Sheets

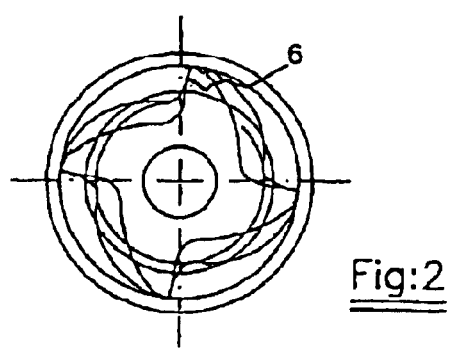
Fig:2
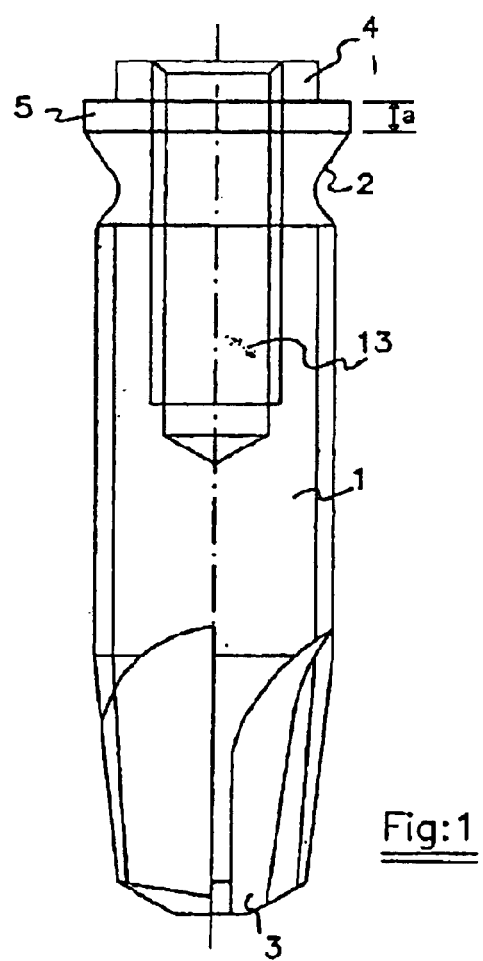
Fig:1
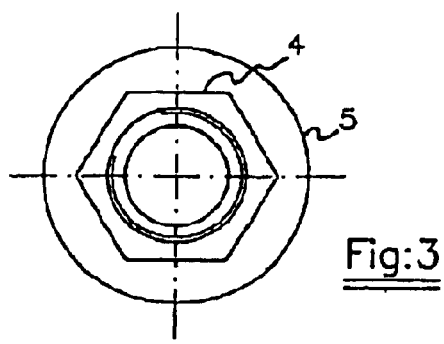
Fig:3

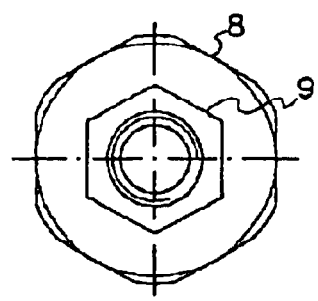
Fig:5
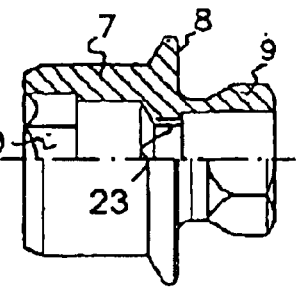
Fig:4
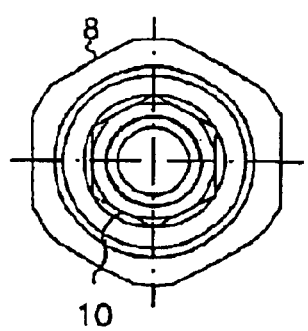
Fig:6
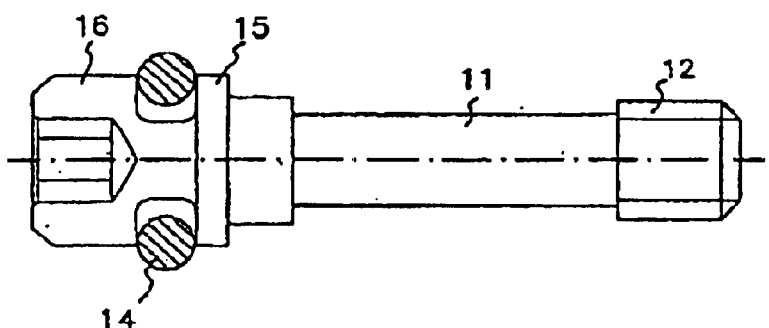
Fig:7
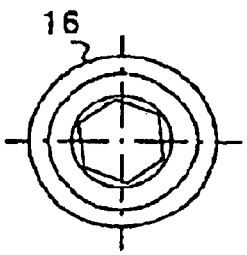
Fig:8
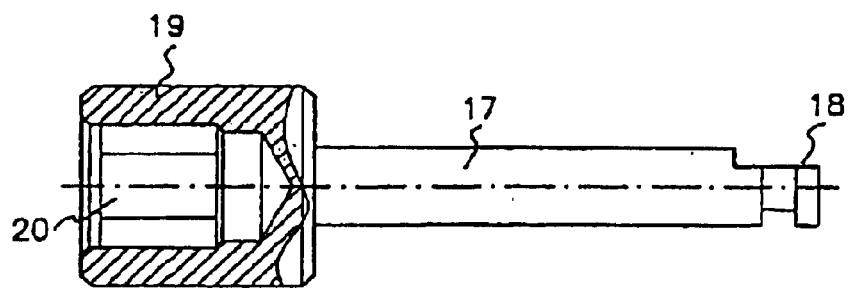
Fig:9
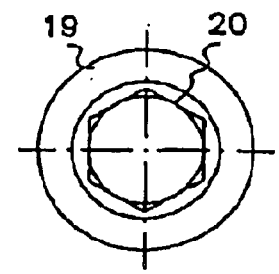
Fig:10

DENTAL IMPLANT-CARRIER ASSEMBLY

FIELD OF THE INVENTION

The invention refers to a dental implant-carrier assembly, which is a set of elements formed by a dental implant plus a series of removable carrier elements. The dental implant that is used is of the type described in reference WO-A-99/18881.

BACKGROUND OF THE INVENTION

With respect to the implant described in WO-A-99/18881, it has been observed that certain features could be improved to increase its initial stability, improve the efficiency of its apical end, and to provide a range of implants that can be used not only for standard applications but also to replace any dental piece.
Carriers used with the mentioned implants; to assist in their installation, have also proved to present several disadvantages.

These carriers consist of three basic parts: a connector, a transporting shaft, and an implant mount connector. The connector is hollow and is fastened to an hexagonal end of the implant. The transporting shaft is a screw that passes through the connector and threads into the internal axial cavity of the implant, keeping the connector in place on the implant. The transporting shaft projects out of the connector forming an abutment to which the implant mount connector is attached.

Existing carriers provide no means of keeping the connection between the transporting shaft and the implant mount connector in place, thus making it difficult to move the implant-carrier assembly without the transporting shaft and implant mount connector falling apart.

In other cases, the connection between the transporting shaft and the implant mount connector is reinforced by mechanical means, which solves the problem mentioned before regarding implant-carrier assembly transportation. The disadvantage of this, however, is that when the implant is correctly installed and the carrier elements must then be removed, it is difficult to extract the implant mount connector, with the risk that if the implant mount connector is then forced the implant may be moved out of position or the initial stability lost.

SUMMARY OF THE INVENTION

It is an object of this invention to provide a dental implant-carrier assembly that manages to:
 increase initial implant stability
 increase implant thread capability
 comprise a variety of implant sizes so that the implants can be adjusted to any dental piece
 facilitate implant transportation and correct positioning
 allow that the carrier acts as a reference during implant installation, so that when several implants are installed, all implants can be positioned with the hexagon in the same position, thus making the orthodontist's work easier.

To achieve these objectives, the implant that showed pairs of cutting edges on its apical is modified by slightly inclining each straight cutting edge. Thus, while in the case of WO-A-99/18881 the straight cutting edge operated in a radial direction in relation to the center of the implant, in the present invention each straight cutting edge maintains its position at its end and leans back at a slight angle, so that it is the aforementioned end that cuts into in the bone initially and advances gradually to make the threading softer and less aggressive. The lean-back angle of these straight cutting edges ranges from 0° to 20°.

In the upper part of the implant, the area connecting the implant head to the threaded section of the implant has a taper of between 50 and 65°. Tests have been carried out that show that this degree of tapering in this area creates greater initial stability once the implant has been threaded in, without causing a significant increase in the distribution of stresses and even decreasing them.

As stated above, the general sizes of the implant are also modified, with the two above-mentioned features being retained as standard features thus creating a standard implant or implant type. Another two implant types are also defined, to be applied to lower incisors and to molars respectively, as well as another one that has been specially designed for hard and very hard bones, which we shall look at in more detail later.

The upper head in the standard implant has a diameter of 4.1 mm, and the upper hexagon measures 2.7 mm between faces and is 0.7 mm high, while the threaded section can have a diameter of 3.3, 3.75 and 4 mm.

The diameter of the incisor implant head is 3.6 mm, and the hexagon measures between 2.4 and 2.6 mm between faces and is 1 mm high. The diameter of the threaded section is 3.3 mm.

The diameter of the molar implant head is 5.5 nun, and the hexagon measures between 2.7 and 3.5 mm between faces and is between 0.7 and 1.2 mm high. The threaded section can have a diameter of 4, 4.5, 5, 5.5 and 6 mm.

It should also be pointed out that the performance of these implants can be improved, particularly when they are used to carry out work on patients with hard or very hard bones, by providing them with a more aggressive and therefore more effective cut, allowing excess bone from the operation to be removed more easily.

According to this invention, the implant is provided with cutting areas that begin right on the flat part of the apical end, and extend outwardly for a certain distance in the radial direction.

The aforementioned cutting areas end some distance before the position corresponding to the base of the tapered threaded section, thus leaving enough space in-between to allow the excess bone to move out normally towards the removal area behind each cutting area, which, in existing implants, is in the form of a tapered convex shape pointing outwards.

Standard sizes have been discovered that will make the aforementioned implant design perform better, all of which are based on the aforementioned features. These sizes refer to the length of the implant, the angles of the tapered threaded sections and the removal areas as well as the length of the implant's tapered threaded sections.

These sizes are adjusted according to the following measurements:

| L | C | α | β |
|---|---|---|---|
| 8.5 | 2.9 | 9° | 4.2° |
| 10 | 2.9 | 9° | 4.2° |
| 11.5 | 4.6 | 5.22° | 3.3° |
| 13 | 4.6 | 5.22° | 3.3° |
| 15 | 4.6 | 5.22° | 3.3° |
| 18 | 4.6 | 5.22° | 3.3° |
| 20 | 4.6 | 5.22° | 3.3° |

L. length of the implant in millimeters.
C. Length of the tapered threaded section in millimeters.
α Angle of the tapered threaded section.
β Angle of the removal area.

The carrier defined by the present invention has two specific features. One of these features is a hexagonal abutment on the outer end of the connector, the position of which matches the position of the hexagonal cavity with which the connector is provided to receive the hexagonal end of the implant.

Thus, when the carrier transports and places the implant in the desired location, the position of the connector's hexagonal abutment will match the position of the hexagonal end of the implant, and therefore act as a reference during implant installation. When installing several implants, the aid of this reference enables the implants to be situated in an identical position, leading to many prosthodontic advantages.

As a second feature, the projecting part of the transporting shaft, which is embraced by the implant mount connector, is provided with an annular neck into which an O-ring seal made of suitable material is fitted. When the implant mount connector embraces the transporting shaft, the O-ring seal keeps the implant mount connector correctly fastened to the transporting shaft, and therefore also to the connector and the implant. Furthermore, the implant mount connector can be removed from the transporting shaft when required without any difficulty whatsoever, without the position and the stability of the implant being affected in any way.

The threaded section of the implant can incorporate a double thread to enable it to be screwed more quickly into the patient's bone.

The speed with which the implant is screwed in will, in any case, depend on the circumstances. The size of the carrier will be adjusted to the size of the implant. Each implant will thus have a corresponding carrier, although the features set out in the invention and described above will be retained.

BRIEF DESCRIPTION OF THE DRAWINGS

These and other aspects of the preferred embodiment of the invention can be seen in greater detail in the drawings attached, details of which are given below:

FIG. 1 is an elevation view of the implant according to the invention.

FIG. 2 is a lower view of FIG. 1.

FIG. 3 is an upper view of FIG. 1.

FIG. 4 is a mid-section elevation view of the one of the carrier's components: the connector.

FIG. 5 is a view of FIG. 4 from the right.

FIG. 6 is a view of FIG. 5 from the left.

FIG. 7 is an elevation view of another of the carrier's components: the transporting shaft.

FIG. 8 is a view of FIG. 7 from the left.

FIG. 9 is an elevation view of another of the carrier's components: the implant mount connector, with a cross-section of the left end.

FIG. 10 is a view of FIG. 9 from the left.

DETAILED DESCRIPTION OF THE DRAWINGS

Figure 12:
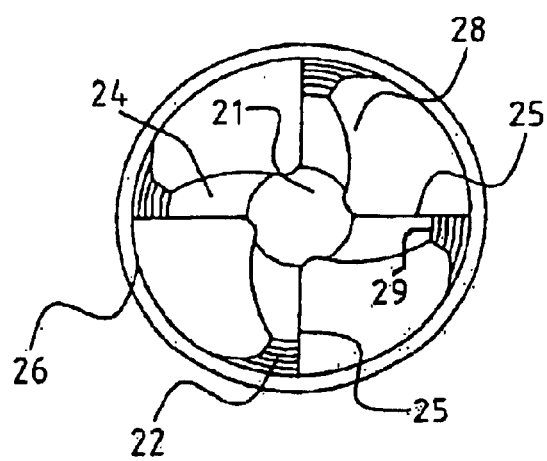
FIG. 12 is a view from above of FIG. 11.

As can be seen in FIGS. 1, 2 and 3, the implant consists of a threaded section (1), an apical end (3), and an upper section comprising the head (5) and the hexagonal end (4), to facilitate its insertion and prosthodontic reconstruction. The head (5) is connected to the threaded section (1) through a tapered section (2), which has a taper of between 48 and 65°, and a cylindrical section with a height (a) of 0.5 mm.

In FIG. 2 we can see the line or straight cutting edge (6) of the apical end. The figure shows that it is separated from the radial position in such a way that the end that is furthest away projects forward to make the cut, and does so by rotating in an anti-clockwise direction according to the position in FIG. 2.

The fact that this cutting edge (6) is inclined at an angle of between 0 and 20° in relation to the radial position and the anti-clockwise direction of the rotation means that it enters more deeply when it begins cutting and does so more gradually and smoothly, but also more effectively, which is the aim of the invention.

In FIG. 1 we can also see the blind threaded hole (13), which extends axially from the hexagonal end (4), with said hole and hexagonal end being the features that are typically used to position the transporting shaft, the connector, and the prosthodontic components.

To achieve this, the connector (7) in FIG. 4 is positioned in such a way that its hexagonal cavity (10) embraces the implant hexagonal end (4), while the transporting shaft (11) in FIG. 7 is introduced through the connector (7), and its threaded end (12) is screwed into the blind threaded hole (13) of the implant. When being introduced, the threaded end (12) of the transporting shaft (11) passes through the internal threaded section (23) of the connector, thus guiding the transporting shaft into place.

In conventional usage of the implant and carrier of the figures, when the connector (7) and the transporting shaft (11) are mounted on the implant, the end (16) of the transporting shaft (11) protrudes outwards. This end (16) is then housed in the interior (20) of the section (19) of the implant mount connector (17) of FIG. 9, so that when a suitable tool is used, for example, connected to the end (18), it moves the implant carrier assembly into the desired position.

By this invention, the connector (7) is provided with the hexagonal parts (8, 9). The position of the faces of these hexagonal parts (8, 9) match the faces of the hexagonal cavity (10) of said connector, and therefore also match the faces of the hexagonal end (4) of the implant.

The fact that the position of the hexagonal faces of the aforementioned parts coincide means that, irrespective of the condition of the implant-carrier assembly, there will always be a valid reference indicating the exact position of the hexagonal end (4) of the implant.

When transporting and placing the dental implant-carrier assembly, the hexagonal base (8) of the connector provides a positional reference. When the implant mount connector (11) is removed, the reference is then provided by the hexagonal parts (8, 9) of said connector (7). In other words, the position occupied by the hexagonal end (4) of the implant will always be able to be identified.

In FIG. 7 we can see that the transporting shaft (11) is provided with the O-ring seal (14), housed in an annular neck between end (16) and abutment (15). When this end (15, 16) is housed in the interior (20) of the implant mount connector (17), the O-ring seal (14) presses against the inner walls of the interior (20) thus keeping the implant-carrier assembly perfectly in position.

Once the implant-carrier assembly has been moved and positioned as desired, the implant mount connector (11) is then removed. The pressure exerted by the O-ring seal (14) allows this to be done easily and smoothly.

These structural modifications enable the dental implant-carrier assembly to provide significantly improved performance, thus meeting the objectives of the invention.

Figure 11:
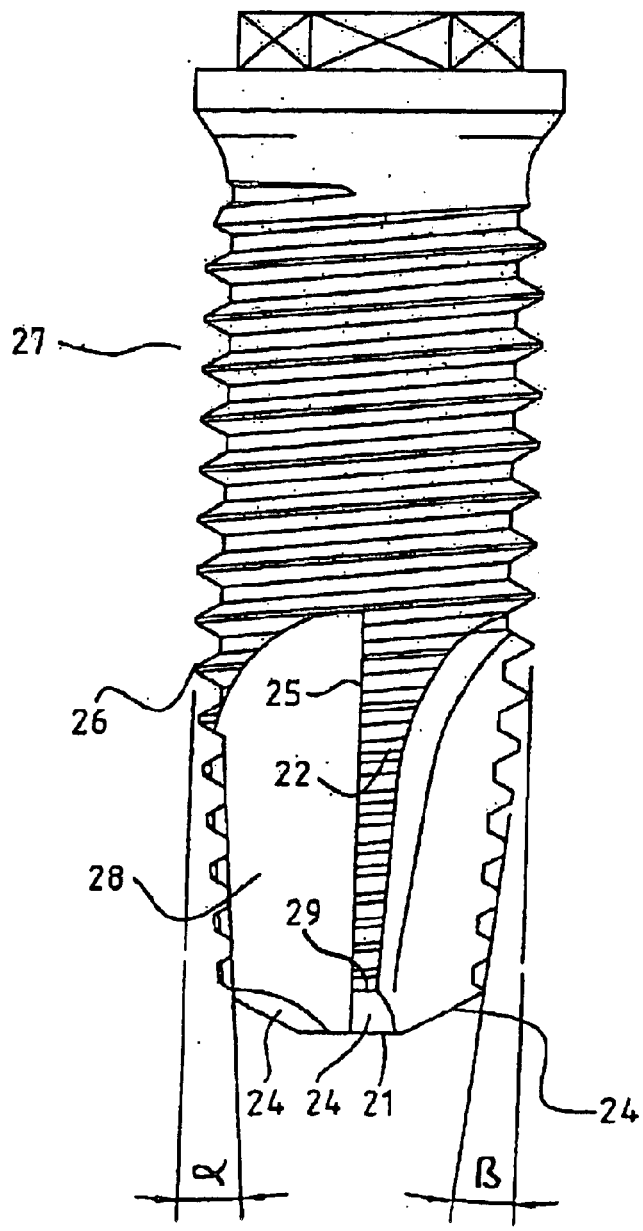
FIG. 11 is an elevation of an implant for hard or very hard bones, according to the invention.

The flat part (21) and four cutting areas (24) present in the apical end of the implant (27) can be seen in FIG. 11. With existing techniques the laterals protrude from the surface of the apical end. The flat part (21) and four cutting areas (24) limit the tapered threaded section (22), which on the opposite side, extends up to the edge (26). The implant runs from this apical end to its opposite hexagonal end, where it connects with the implant manipulating tool (carrier, etc.). The head and the hexagonal end of the implant, which are not numbered, can be seen at this opposite end.

As detailed in FIG. 12, we can see the four cutting areas (24), which radiate out from the flat part (21) until they reach a circular section (29) at a certain distance from the edge (26). This distance provides a gap through which the cut bone is directed to the removal area (28) behind the cutting areas (24).

As can be seen in FIGS. 11 and 12, the tapered threaded section (22) runs from the circular section (29) and vertical wall (25), towards the tapered convex removal area (28).

The angles ($\alpha$) and ($\beta$) in FIG. 11 determine the measurements of the taper of the tapered threaded section (22) and the removal area (28).

As the implant head has diameters of 4.1 mm or 5.5 mm and the hexagon can protrude above this head by 0.7 mm or between 0.7 and 1.2 mm, the invention can evidently be applied to the technique outlined in the reports quoted at the beginning of this document.

What is claimed is:

1. A dental implant-carrier assembly, designed to facilitate dental implant transportation and installation, that comprises:

a dental implant comprising a threaded section, an apical end having at least one straight cutting edge, a head, a hexagonal end protruding out of the head, and a blind threaded cavity; and a carrier comprising a connector, a transporting shaft and an implant mount connector, wherein the connector is mounted on the hexagonal end, the transporting shaft comprises a threaded end that passes through the connector and is screwed into the implant blind threaded hole, and the transporting shaft comprises a free end that is operated by the implant mount connector, wherein the area connecting the implant head to the threaded section of the implant has a taper of between 48 and 65°;

the straight cutting edge of the apical end of the implant is inclined relative to a radial position and behind the radial position in a direction of movement of the cutting edge at an angle of greater than 0° and less than or equal to 20°, wherein the outermost end of the cutting edge is the part that first makes contact with the area to be cut;

the connector comprises an abutment comprising a hexagonal abutment situated on a hexagonal base, the sides of the hexagonal abutment and the hexagonal base being in line with each other and with the faces of the hexagonal end of the implant;

the connection between the implant mount connector and the transporting shaft comprises an O-ring seal positioned at the projecting end present in one of the parts of the connection, the projecting end being housed in a cavity present in another one of the parts of the connection.

2. A dental implant-carrier assembly, according to claim 1, wherein in its application to incisors, the diameter of the implant head is 3.6 mm, the hexagonal end measures between 2.4 and 2.6 mm between faces and is 1 mm high, and the diameter of the threaded section is 3.3 mm.

3. A dental implant-carrier assembly, according to claim 1, wherein in its application to molars, the diameter of the implant head is 5.5 mm, the hexagonal end measures between 2.7 and 3.5 mm between faces and is between 0.7 and 1.2 mm high, and the threaded section can have a diameter of 4, 4.5, 5, 5.5 or 6 mm.

4. A dental implant-carrier assembly, according to claim 1, wherein the dental implant comprises cutting areas that radiate out from a flat part on the apical end, that create respective vertical walls, and that are crowned by circular sections from which the tapered threaded implant begins, the taper of the exterior of threaded section is determined by a generator angle ($\beta$) of between 9 and 5.21°, in relation to the vertical, while the generator angle ($\alpha$) of the taper of the interior of the threaded section is set at between 4.2 and 3.3° in relation to the vertical, with these values being adjusted to total implant lengths ranging from 8.5 to 20 mm and to the lengths of the tapered threaded section, which range from 2.9 to 4.6 mm.

5. A dental implant-carrier assembly, according to claim 1, wherein the sizes of the carrier are adjusted according to each implant.

6. A dental implant-carrier assembly, according to claim 1, wherein a standard implant comprises a head with a diameter of 4.1 mm, a hexagonal end that measures 2.7 mm between faces and is 0.7 mm high, and a threaded section that has a diameter of 3.3, 3.75 or 4 mm.

* * * * *